(12) United States Patent
Finn et al.

(10) Patent No.: US 10,517,491 B2
(45) Date of Patent: Dec. 31, 2019

(54) CARDIAC PHASE-RESOLVED NON-BREATH-HOLD 3-DIMENSIONAL MAGNETIC RESONANCE ANGIOGRAPHY

(71) Applicant: THE REGENTS OF THE UNIVERSITY OF CALIFORNIA, Oakland, CA (US)

(72) Inventors: J. Paul Finn, Los Angeles, CA (US); Peng Hu, Beverly Hills, CA (US); Fei Han, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 206 days.

(21) Appl. No.: 15/346,036

(22) Filed: Nov. 8, 2016

(65) Prior Publication Data
US 2017/0273578 A1 Sep. 28, 2017

Related U.S. Application Data

(63) Continuation of application No. PCT/US2015/030015, filed on May 8, 2015.
(Continued)

(51) Int. Cl.
*A61B 5/026* (2006.01)
*A61B 5/00* (2006.01)
*G01R 33/56* (2006.01)
*G01R 33/563* (2006.01)
*G01R 33/567* (2006.01)
(Continued)

(52) U.S. Cl.
CPC .......... *A61B 5/0263* (2013.01); *A61B 5/0402* (2013.01); *A61B 5/055* (2013.01); *A61B 5/113* (2013.01); *A61B 5/7285* (2013.01); *A61K 49/1818* (2013.01); *A61M 5/007* (2013.01); *A61M 16/0003* (2014.02); *G01R 33/5601* (2013.01); *G01R 33/5635* (2013.01); *G01R 33/5673* (2013.01); *A61B 2503/06* (2013.01); *A61M 2016/0027* (2013.01);
(Continued)

(58) Field of Classification Search
USPC ....................................................... 463/413
See application file for complete search history.

(56) References Cited

U.S. PATENT DOCUMENTS

| 7,689,263 B1 | 3/2010 | Fung et al. |
| 2003/0157020 A1* | 8/2003 | Petersson ........... G01R 33/5601 424/9.3 |

(Continued)

FOREIGN PATENT DOCUMENTS

| DE | 102008032827 A1 | 1/2010 |
| JP | 2008-148806 A | 8/2008 |

OTHER PUBLICATIONS

Ennis, et al., Respiratory and Cardiac Gated 3D Imaging for Improved Spatial and Temporal Resolution, Proc. Intl. Soc. Mag. Reson. Med., 2002, 10, 1 page.
(Continued)

*Primary Examiner* — Pierre E Elisca
(74) *Attorney, Agent, or Firm* — Quarles & Brady LLP

(57) ABSTRACT

3D cine MR angiography systems and methods are disclosed for use during the steady state intravascular distribution phase of ferumoxytol. The 3D cine MRA technique enables improved delineation of cardiac anatomy in pediatric patients undergoing cardiovascular MRI.

28 Claims, 6 Drawing Sheets

Related U.S. Application Data

(60) Provisional application No. 61/990,776, filed on May 9, 2014.

(51) Int. Cl.
    *A61B 5/055*     (2006.01)
    *A61M 16/00*     (2006.01)
    *A61B 5/0402*     (2006.01)
    *A61B 5/113*     (2006.01)
    *A61K 49/18*     (2006.01)
    *A61M 5/00*     (2006.01)
    *G01R 33/561*     (2006.01)
    *G01R 33/48*     (2006.01)

(52) U.S. Cl.
    CPC ...... *G01R 33/4822* (2013.01); *G01R 33/5616* (2013.01); *G01R 33/56325* (2013.01)

(56) References Cited

U.S. PATENT DOCUMENTS

| | | |
|---|---|---|
| 2003/0233039 A1 | 12/2003 | Shao et al. |
| 2004/0030234 A1 | 2/2004 | Hayek |
| 2005/0187464 A1* | 8/2005 | Ho .................. A61B 5/055 600/428 |
| 2007/0253910 A1* | 11/2007 | Ahrens ............... A61B 5/411 424/9.34 |
| 2008/0280866 A1* | 11/2008 | Hauser ............. A61K 31/4422 514/186 |
| 2013/0338489 A1* | 12/2013 | Prisk ................. A61B 5/055 600/420 |
| 2014/0112566 A1* | 4/2014 | Steinberg ........... A61B 5/0044 382/131 |
| 2015/0283319 A1* | 10/2015 | Tolkowsky ........... A61B 90/37 600/431 |

OTHER PUBLICATIONS

Grove, et al., Modified Ventilator with Logic Controller for Cardiorespiratory Synchronisation of Magnetic Resonance Imaging in Small Animals, Medical & Biological Engineering & Computing, 1995, 33(1):104-107.

Han, et al., Four-Dimensional, Multiphase, Steady-State Imaging with Contrast Enhancement (MUSIC) in the Heart: A Feasibility Study in Children, Magnetic Resonance in Medicine, 2015, 74:1042-1049.

Henningsson, et al., Contrast-Enhanced Specific Absorption Rate-Efficient 3D Cardiac Cine with Respiratory-Triggered Radiofrequency Gating, Journal of Magnetic Resonance Imaging, 2013, 37:986-992.

Prince, et al., A Pilot Investigation of New Superparamagnetic Iron Oxide (ferumoxytol) as a Contrast Agent for Cardiovascular MRI, Journal of X-Ray Science and Technology, 2003, 11:231-240.

Schmidt, Advanced Motion Correction and Image Reconstruction for Cardiac Magnetic Resonance, Doctoral Thesis, ETH Zurich, 2013, 132 pages.

European Patent Office, Extended European Search Report, Application No. 15789422.1, dated Dec. 18, 2017, 12 pages.

Korean Intellectual Property Office (KIPO), International Search Report and Written Opinion, dated Aug. 21, 2015, related PCT International Application No. PCT/US2015/030015, pp. 1-14, with claims searched, pp. 15-18. The relevance of non-English language JP 2008-148806 is indicated in this search report and a separate written explanation if the relevance is not required.

\* cited by examiner

First-pass
Breath-held MRA

3D Cine MRA

Delayed Phase
Breath-held MRA

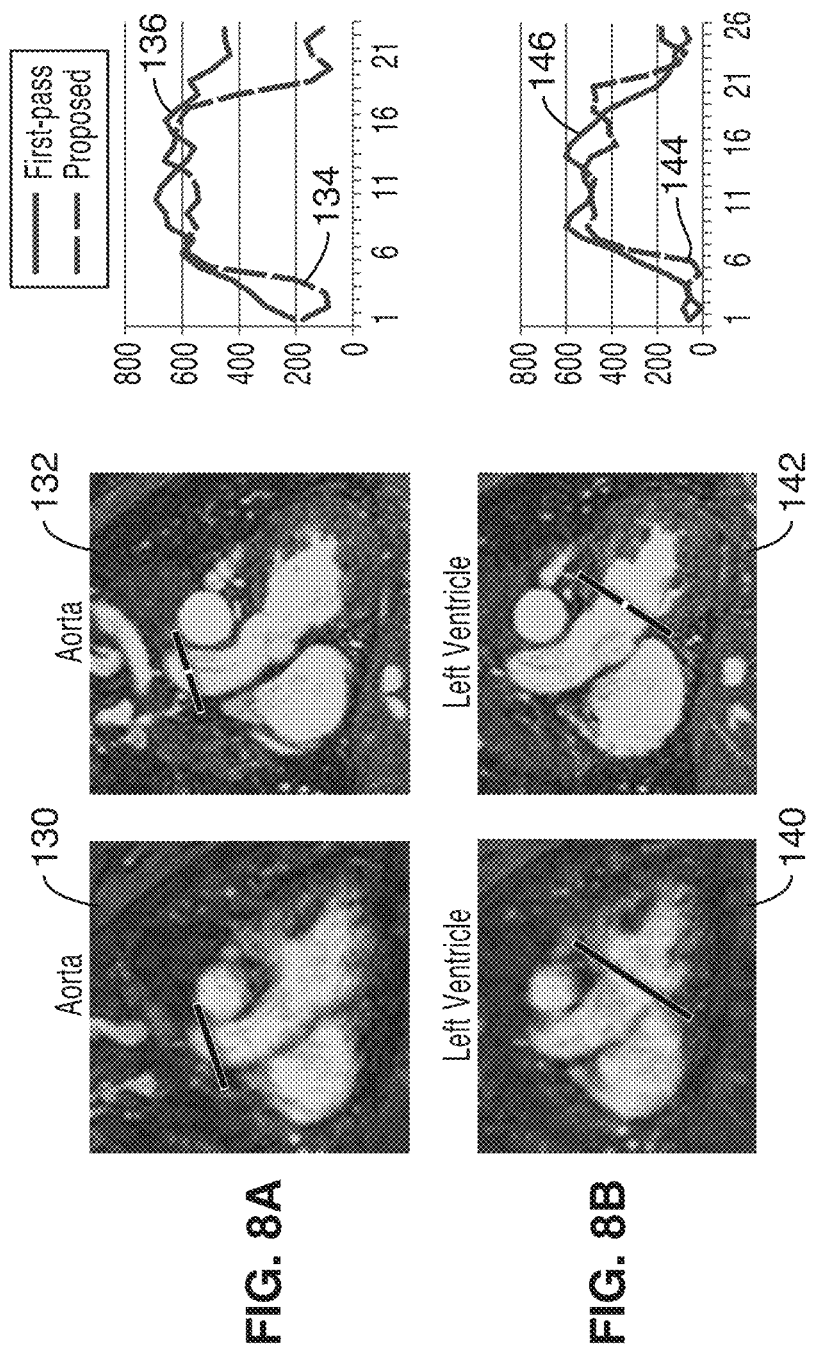

CARDIAC PHASE-RESOLVED NON-BREATH-HOLD 3-DIMENSIONAL MAGNETIC RESONANCE ANGIOGRAPHY

CROSS-REFERENCE TO RELATED APPLICATIONS

This application is a 35 U.S.C. § 111(a) continuation of PCT international application number PCT/US2015/030015 filed on May 8, 2015, incorporated herein by reference in its entirety, which claims priority to, and the benefit of, U.S. provisional patent application Ser. No. 61/990,776 filed on May 9, 2014, incorporated herein by reference in its entirety. Priority is claimed to each of the foregoing applications.

The above-referenced PCT international application was published as PCT International Publication No. WO 2015/172100 on Nov. 12, 2015, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This invention pertains generally to angiography, and more particularly to 3D magnetic resonance imaging angiography.

2. Background Discussion

Contrast-enhanced magnetic resonance angiography (CE-MRA) is particularly appealing for evaluating patients with cardiovascular disorders due to concerns associated with alternative imaging modalities, including repeated exposure to ionizing radiation, invasive catheterization and the use of iodinated contrast agents. Detailed delineation of the vascular anatomy provided by CE-MRA is important for planning surgical or catheter interventions.

Conventional breath-hold first-pass CE-MRA provides diagnostic visualization of the majority of extra-cardiac vessels. However, first-pass CEMRA is generally applied without cardiac gating and provides limited or poor definition of intra-cardiac anatomy, e.g. ventricular outflow tracts, cardiac chambers and coronary anatomy, such that supplemental 2-D cardiac cine MRI is usually required. Cardiac gated 3D CEMRA has been described previously, but the requirement to image the first pass of a contrast bolus in a breath-hold has imposed restrictions on temporal resolution, spatial resolution and anatomic coverage, relative to their non-gated counterparts.

Furthermore, patients younger than 6 years old are generally unable to cooperate with breath-hold instructions. Therefore, in several institutions, general anesthesia and mechanical ventilation are preferred in these young patients where a controlled breath-hold is achieved by temporarily pausing the MR-compatible ventilator. Breath holding is repeated for several temporal phases of contrast enhancement and also for multiple, individual cardiac cine acquisitions. For the vast majority of patients, controlled apnea is a very safe procedure when carried out by specialist anesthesiologists or neonatal intensive care unit (NICU) staff. Nonetheless, in sick infants and neonates with complex congenital heart disease (CHD), it is desirable to minimize the frequency and duration of breath holding, while at the same time providing sufficiently detailed anatomic and functional evaluation of the heart and great vessels to guide patient management.

Moreover, in infants and patients with severe renal impairment, concerns about nephrogenic systemic fibrosis (NSF) and warnings from the Food and Drug Administration (FDA) have caused referring physicians to shy away from the use of GBCAs.

CE-MRA is typically performed within a breath-hold of 20-25 seconds during first pass of a gadolinium based contrast agent (GBCA). Due to the limitation in breath-hold time and first-pass of the contrast agent, these acquisitions are generally not gated to cardiac ECG signal and those that are gated sample only a single phase of the cardiac cycle. As a result, the conventional CE-MRA falls short in providing detailed definition of intra-cardiac anatomy, such as the cardiac chambers, the coronary blood vessels, the valves, etc. This is particularly limiting for children with congenital heart diseases, where high resolution imaging of anatomy and function is crucial.

For example, patients younger than 6 years old are generally unable to cooperate with breath-hold instructions. Therefore, general anesthesia and mechanical ventilation are preferred in these young patients where a controlled breath-hold is achieved by temporarily pausing the MR-compatible ventilator. Breath holding is repeated for several temporal phases of contrast enhancement and also for multiple, individual cardiac cine acquisitions. For the majority of patients, controlled apnea is a safe procedure when carried out by specialist anesthesiologists or neonatal intensive care unit (NICU) staff. Nonetheless, in sick infants and neonates with complex congenital heart disease (CHD), it is desirable to minimize the frequency and duration of breath holding, while at the same time providing sufficiently detailed anatomic and functional evaluation of the heart and great vessels to guide patient management.

BRIEF SUMMARY

An aspect of the present description is cardiac phase-resolved non-breath-hold 3D magnetic resonance angiography that is performed during the steady state distribution phase of intravascular contrast agents, such as ferumoxytol. This provides highly detailed definition for both intra-cardiac and extra-cardiac anatomy that has not been possible using the conventional breath-held first-pass contrast-enhanced MRA techniques.

In one aspect, the use of ferumoxytol as an intravascular contrast agent, in conjunction with a 3D cine MRA sequence and ventilator respiratory gating, enables high quality delineation of cardiovascular anatomy beyond what is currently possible using conventional cardiovascular MRI in pediatric patients.

The data acquisition methods of the present description may be performed without the need for breath holding, because the concentration of the intravascular contrast agent, such as ferumoxytol, is highly stable within the blood pool, once the steady state distribution phase has been established. This is in sharp distinction to the case with the conventional gadolinium based extracellular contrast agents, which are eliminated rapidly by the kidneys and are also diluted by distribution into the expansive extracellular fluid space. These attributes of the extracellular contrast agents limit their useful angiographic time window to the first-pass and very early distribution phases.

One particular embodiment is a use case for pediatric patients who are referred for cardiac MRI under general anesthesia with controlled mechanical ventilation. In this scenario, the respiratory rate and rhythm are regular and controlled and data acquisition is performed using, for example, the ventilator airway pressure signal as a respiratory motion gating signal. Other tools to exploit the regularity of the ventilator respiratory pattern can readily be used. Without the need for breath-holding or the need to acquire data during the first-pass of the contrast agent, the acquisition can last several minutes while it is gated, not just to the respiratory signal but also to the cardiac ECG signal. Hence it is a segmented acquisition analogous to traditional cardiac cine MRI and can be used to provide not just anatomic information, but also dynamic, functional imaging of the heart in three dimensions, with the capability to reformat planes in any orientation and with unprecedented spatial resolution for a cardiac cine study.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 8A and FIG. 8B show plots and corresponding images illustrating vessel sharpness measurements for lines crossing the ascending aorta and left ventricle in corresponding left ventricle and aorta images.

DETAILED DESCRIPTION

Figure 1:
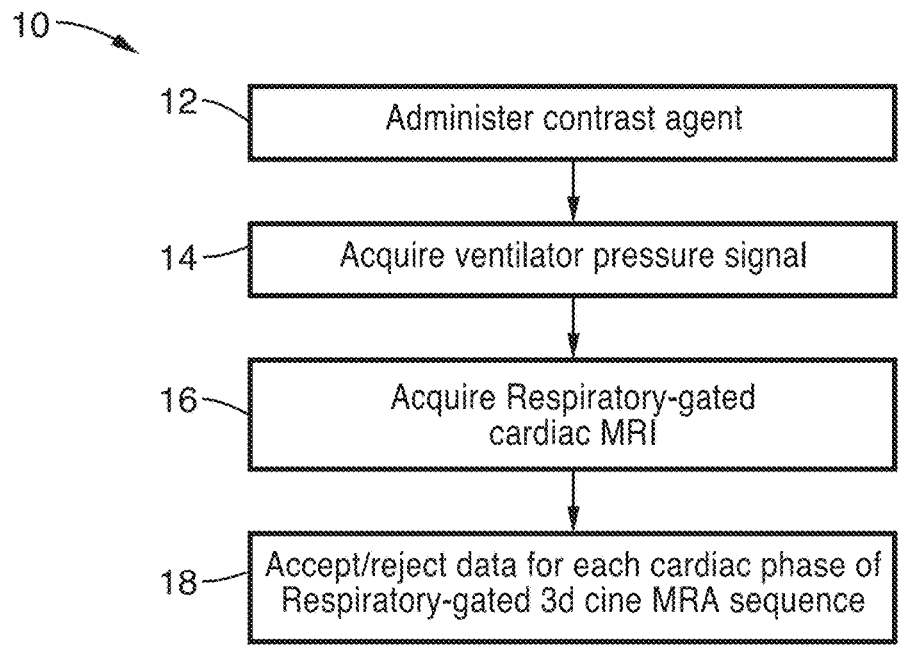
FIG. 1 shows a flow diagram illustrating the respiratory-gated 3D CINE MRA method of the present description.
Figure 2:
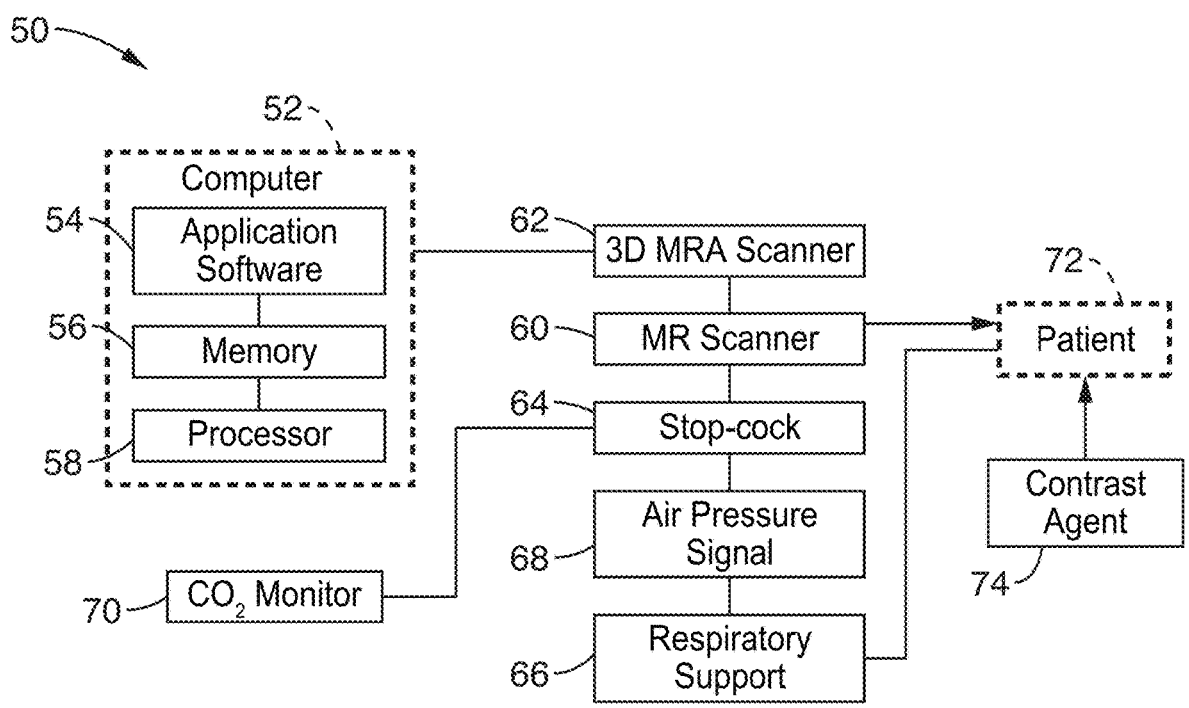
FIG. 2 is a schematic system diagram of the respiratory-gated 3D CINE MRA system of the present description.

FIG. 1 shows a flow diagram illustrating the respiratory-gated 3D CINE MRA method 10 of the present description. The method may be implemented via a respiratory-gated 3D CINE MRA system 50 as illustrated in FIG. 2. First, the contrast agent 74 is administered to the patient 72 at step 12. As will be explained in further detail below, the contrast agent 74 preferably comprises a specifically selected agent having a high T1 relaxivity, long intra-vascular half-life, and is not readily eliminated (e.g. by normal kidney function).

Next, at step 14, a ventilator airway pressure signal 68 is acquired from respiratory support device 66 (e.g. ventilator or the like). In one embodiment, the air pressure signal 68 may be tapped into a respiratory circuit (not shown) in the mechanical ventilatory support device 66 via a 3-way stopcock 64 and fed in real time into the MR scanner 60 (e.g. the scanner's physiological monitoring unit) for respiratory gating. Thus 3D MRA sequence data 62 acquisition may be performed at step 16 using the ventilator air way pressure signal 68 as a respiratory motion gating signal. Without the need for breath-holding or the need to acquire data during the first-pass of the contrast agent 74, the acquisition can last several minutes while it is gated, not just to the respiratory signal 68 but also to the cardiac ECG signal. The other limb of the stop-cock 64 may be input to an end-tidal $CO_2$ monitor 70 (e.g. InVivo Research, Orlando, Fla.).

Next at step 18, the acquired data is accepted or rejected for each cardiac phase of the respiratory-gated 3D CINE MRA sequence, as shown in more detail below with respect to FIG. 3. Programming for executing steps 14 through 16 may be performed via internal processing on the MIR scanner 60, or a dedicated computer 52 having application software 54 stored in memory 56 for execution on processor 58.

In a preferred embodiment, the contrast agent 74 comprises ferumoxytol. Ferumoxytol is an ultra-small superparamagnetic iron oxide (USPIO) particle, marketed in the U.S. as Feraheme (AMAG Pharmaceuticals, Cambridge, Mass.) and approved by the U.S. FDA as an iron supplement for patients with chronic kidney disease. Aside from its use as an iron supplement, ferumoxytol has excellent potential as a diagnostic imaging agent due to several desirable properties. First, it has much higher T1 relaxivity ($r_1$=15.7 mM$^{-1}$second$^{-1}$ at 1.5 tesla) compared to conventional extracellular GBCA. Second, due to its larger particle size, it is a blood pool contrast agent with an intravascular half-life of 10-14 hours. In addition, unlike GBCA, the particles are not eliminated by the kidney and are not known to be associated with NSF, making it an excellent alternative to GBCA for patients with impaired kidney function. While ferumoxytol is a preferred agent, it is appreciated that other agents, (e.g. GBCAs) may also be implemented where appropriate.

The technology described herein provides a technique that exploits the intravascular temporal stability and relaxivity of ferumoxytol in children, without the need for breath-holding. By acquiring high-resolution data in multiple phases of the cardiac cycle, structures within and around the heart, which are typically subject to motion degradation in ungated acquisitions, are clearly defined with the systems and methods of the present description. The 3D cine MRA data 62 thereby acquired via the systems and methods of the present description may be used to support detailed visualization of intra-cardiac anatomy and dynamics in arbitrary planes.

Figure 3:
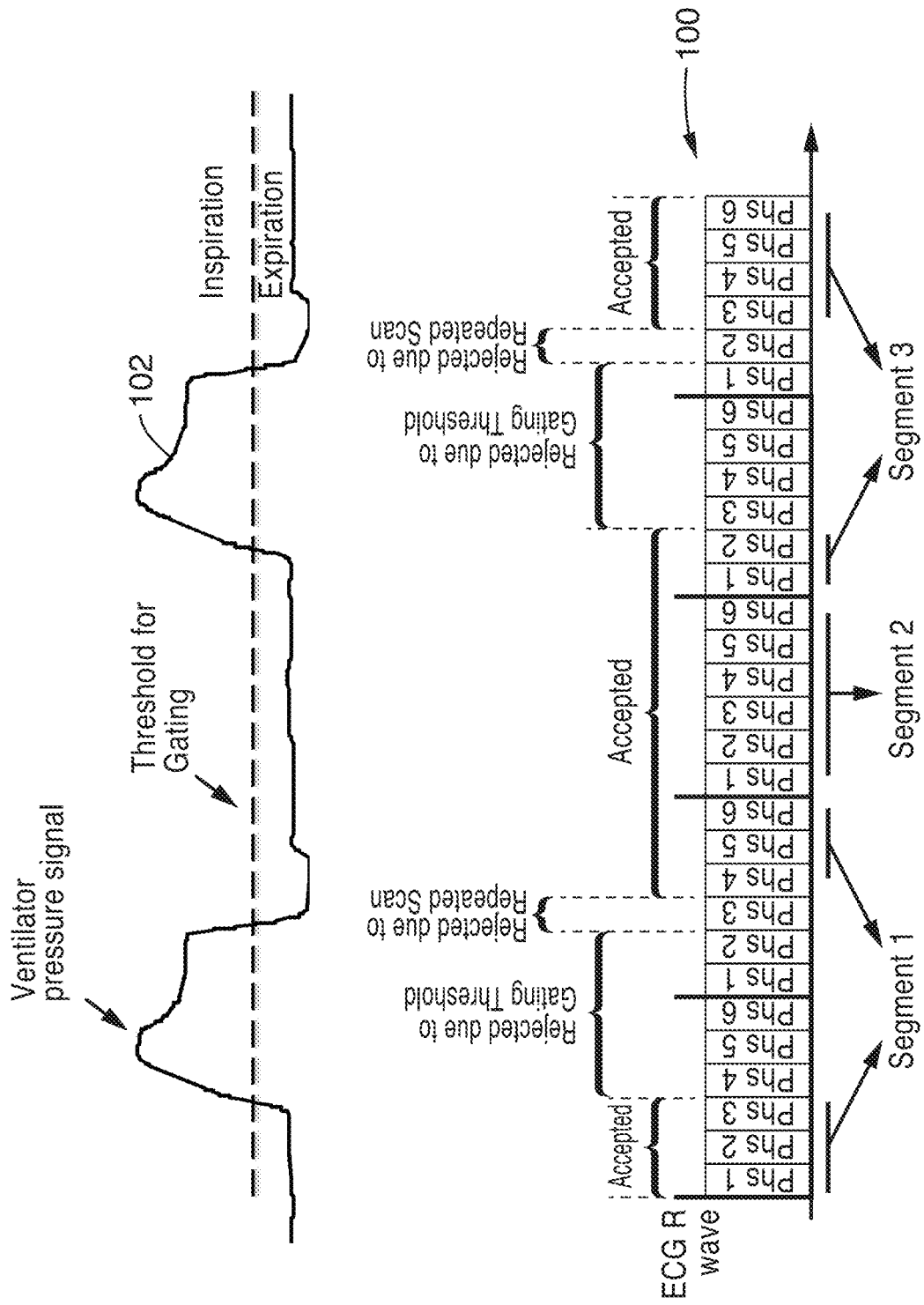
FIG. 3 is a schematic diagram illustrating the respiratory-gated 3D CINE MRA sequence utilizing the airway pressure signal for respiratory gating in accordance with the present description.

FIG. 3 shows a schematic diagram illustrating the respiratory-gated 3D CINE MRA sequence 100 utilizing the airway pressure signal 102 for respiratory gating in accordance with the present description. The decision of accepting or rejecting data is made for each cardiac phase (Phs) of the respiratory-gated 3D CINE MRA sequence 100 (shown in FIG. 3 with 6 phases per heartbeat (HB), instead of each R-R interval, yielding improved gating efficiency. FIG. 3 shows a piece of the actual ventilator pressure signal 102 and data acquisition timing recorded from an exemplary subject patient. In this example, Phs4-6 in HB1 and Phs1-2 in HB2 were rejected because the ventilator pressure registered above the gating threshold. Phs3 in HB2 was also rejected because the same data has already been acquired in the first heartbeat. The accepted data in HB1 and HB2 is combined as a complete segment (Segment 1), even though neither HB is completely within the respiratory gating window. The gating efficiency in this example was 60% (3 out of 5 heartbeats) although only 1 heartbeat was entirely within the respiratory gating window.

The sequence 100 of FIG. 3 is configured as a high bandwidth, 3D, ECG-triggered spoiled gradient echo sequence. The 3D data acquisition is configured such that k-space is segmented in a fashion analogous to 2D cardiac cine MRI, whereby 5-8 independent temporal phases (6 shown in FIG. 3) are acquired within the cardiac cycle. Instead of accepting or rejecting data for the entire R-R interval as previously proposed, the gating acceptance/rejection decision in step 18 is made for each individual cardiac phase to improve the gating efficiency, as shown in FIG. 3.

Although the systems and methods disclosed herein are primarily directed to cardiac MRI for pediatric patients under general anesthesia and controlled mechanical ventilation, it is appreciated that the techniques disclosed herein may be implemented for other patients (pediatric or adult) who undergo cardiac MRI during spontaneous breathing without general anesthesia.

Example 1

Six patients (mean age 2.4±2.1 y.o., range 3 days to 5 years, 4 male) underwent cardiovascular MRI with controlled mechanical ventilation. Conventional breath-held contrast-enhanced MRA (CE-MRA) was performed during the first-pass in comparison to delayed steady state distribution phases of ferumoxytol, which was used in place of gadolinium based contrast agents (GBCA).

Four patients underwent general anesthesia and 2 patients were transferred already intubated from the neonatal intensive care unit (NICU) and the patients were monitored by pediatric anesthesiologists or NICU staff respectively, who monitored the patients continuously throughout the imaging exam. As appropriate, anesthesia was maintained with inhalation of a mixture of oxygen and savoflurane and patients from the NICU were sedated with fentanyl. In all cases, 0.2 mg/kg of Rocuronium Bromide was administrated as a muscle relaxant. An MR compatible ventilator (Fabius MRI, Drager Medical, Telford, Pa.) was used with positive end expiratory pressure (PEEP) in select cases as considered clinically appropriate. Standard physiologic monitoring was performed (ECG, pulse oximetry, blood pressure and end-tidal $C_{O2}$ level) with an MR compatible monitoring system (InVivo Research, Orlando, Fla.).

All studies were performed on a clinical whole body 3 T MRI scanner (Magnetom TIM Trio, Siemens Medical Solutions). Receiver coil configurations were customized to patient size and included adult knee coil, head coil, flex coil or body array coil and these were combined if appropriate, depending on the size of the subject to provide optimal coverage.

For each patient, ferumoxytol was administered to a dose of 4 mg/kg of iron. The product formulation was diluted to a volume such that the infusion period was 15 seconds at the flow rate considered appropriate for patient size (0.3-1.0 ml/s). A small timing bolus containing 0.5 mg/kg iron was first injected to determine the delay time between injection and the arrival of contrast in the region of interest, similar to a conventional timing test injection with GBCAs. After the correct timing for the first-pass CE-MRA sequence was obtained, the remaining bolus was injected at the rate of 0.3-1.0 ml/s (adjusted based on the patient size) followed by a bolus of saline administered at the same infusion rate. A first-pass CE-MRA acquisition spanning an 18-22 second breath-hold was performed. Subsequently, the same acquisition was repeated during the delayed venous phase of ferumoxytol.

Parameters for first-pass and delayed phase CE-MRA were as follows: TR/TE=2.9/0.9 ms; flip angle, 15°; in-plane resolution, 0.9-1.2 mm; slice thickness, 1.1-1.5 mm; GRAPPA acceleration 3×-4×. Partial Fourier acquisition was used for in-plane and through-plane phase encoding directions. The ventilator gated, 3D-cine MRA acquisition was started during the steady state distribution phase of ferumoxytol, 3-5 minutes following the first pass acquisition. Depending on the patient's heart rate, 5-8 cardiac phases were acquired. The respiratory gating window was positioned in the expiration phase and a threshold was set to 30% of the signal's dynamic range, such that data were acquired only when the airway pressure signal was below the predefined threshold. Sequence parameters included: TR/TE=2.9/0.9 ms; flip angle, 15°; 3D isotropic resolution, 0.6-0.9 mm; GRAPPA 2×-3× and partial Fourier was used in phase encoding and partition encoding direction. For heart rates in the 110 bmp to 160 bpm range, each of the 5-8 cardiac phases was acquired within a time window of 65 ms to 95 ms.

Visual assessment of the subjective image quality was performed by two board-certified radiologists. The conventional breath-held CE-MRA images and the proposed cine CE-MRA images were presented in random order to the evaluators, who were blinded to the patient information and the imaging technique. The evaluators scored the images on a 1-4 scale (1: non-diagnostic; 2: poor definition such that only gross features such as overall patency are evaluable; 3: good definition such that pathology can be confidently visualized or excluded; 4: excellent definition such that detailed anatomy is clearly visualized with sharp borders) with respect to aortic root, pulmonary trunk, myocardium (left and right ventricles), coronary artery origin and descending aorta.

Quantitative analysis of the first-pass breath-held CE-MRA and the cine CE-MRA were performed. Signal to noise ratio (SNR) was measured as the mean signal in an ROI of the aortic arch divided by the standard deviation of an ROI of air outside of the patient's body. Sharpness was measured in the left ventricle and ascending aorta by drawing a linear signal profile and calculating the slope of the signal intensity. The slope is defined as the image intensity difference divided by the distance between the two points at 20% and 80% of the dynamic range respectively. The calculated slope on both sides was then averaged as the final sharpness measurement.

The SNR and vessel sharpness measurements of the two images were compared using a paired t-test. The subjective image quality scores were compared using a Wilcoxon signed-rank test. For both tests, a P<0.05 is considered statistically significant.

The 3D cine CE-MRA method described herein was successfully acquired on all 6 subjects, with the scan time ranging from 3.5 minutes to 8 minutes, and the respiratory gating efficiency ranging from 45%-58%. The breath-held first-pass CE-MRA was not acquired in 2 patients, due to concerns about cardiopulmonary insufficiency.

Figure 4:
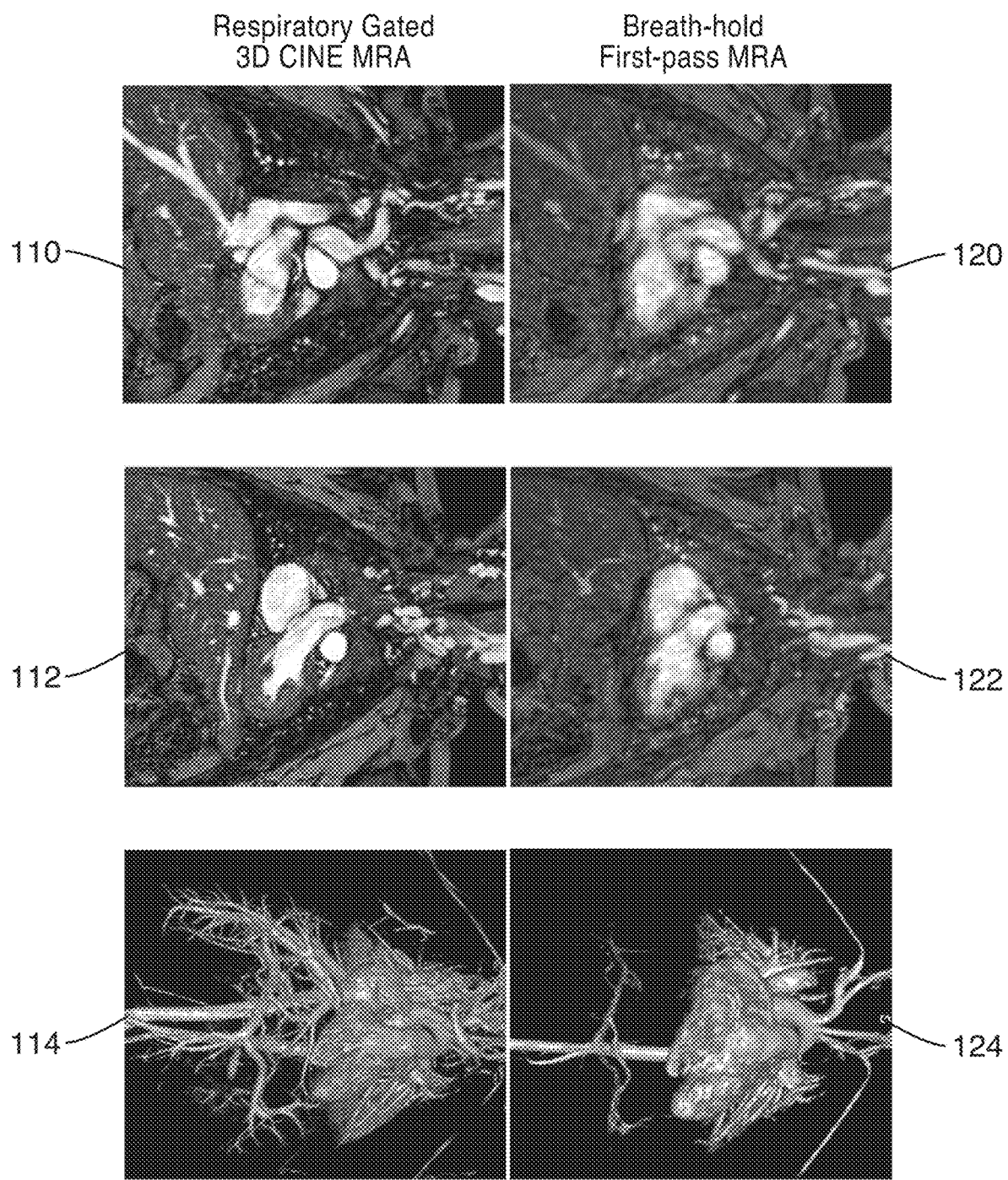
FIG. 4 shows images of conventional breath-hold first-pass CE-MRA vs. proposed respiratory-gated 3D cine MRA (phase #3 is chosen out of 5 cardiac phases for display) of a 4-year-old, 10 kg boy.

FIG. 4 shows a comparison of two images of conventional first-pass breath-held CE-MRA (images 120 and 122) and the 3D cine MRA method of the present disclosure (images 110 and 112) as well as comparison images (124 vs. 114) for 3D volume rendering of a patient. Due to lack of cardiac gating, the anatomy of the ventricles and atria in the breath-held first-pass CE-MRA image 124 was blurred by cardiac motion, and the definition of the proximal great vessels was also compromised. However, these structures, as well the coronary arteries (and in particular the proximal coronary artery), were clearly defined (sharper vessel edges and blood-myocardium boundaries) without motion-related blurring using the 3D cine MRA generated image 114.

Figure 5:
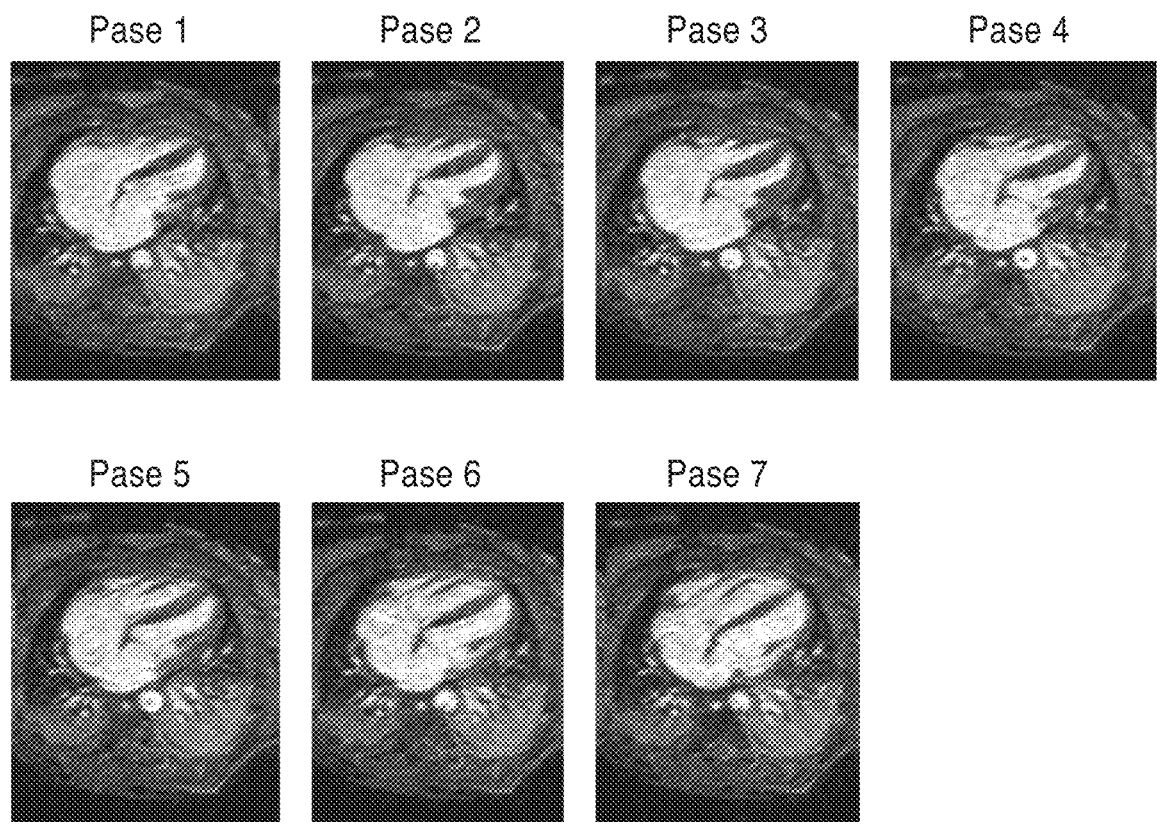
FIG. 5 shows reformatted cardiac four chamber view images based on the 3D cine MRA performed on a 3-day-old patient in accordance with the present disclosure.

FIG. 5 shows reformatted cardiac four-chamber view images based on the 3D cine MRA data acquired on a 3-day-old 2 kg boy. Due to concerns about cardiopulmonary insufficiency, the attending anesthesiologist advised against breath-holding during the MRI scan. As a result, neither standard breath-hold first-pass MRA nor 2D breath-hold cardiac cine MRI was acquired on this patient. However, the ventricular anatomy, chamber size, and myocardial thickness were able to be assessed based on the 7 cardiac phases MRA images, which spanned the cardiac cycle. The cardiac chambers are well delineated for both systole and diastole phases of the cardiac cycle. Arbitrary reconstruction planes are possible without loss of resolution due to the 0.7 mm isotropic resolution in this patient.

Figure 6A:
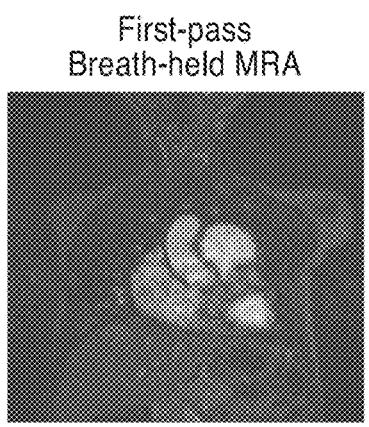
FIG. 6A through FIG. 6C are images illustrating a comparison of first-pass (FIG. 6A), 3D cine MRA (FIG. 6B), and delayed phase breath-held MRA (FIG. 6C) acquired from a 3-year-old 14 kg girl with an aneurysmal pulmonary artery.
Figure 6B:
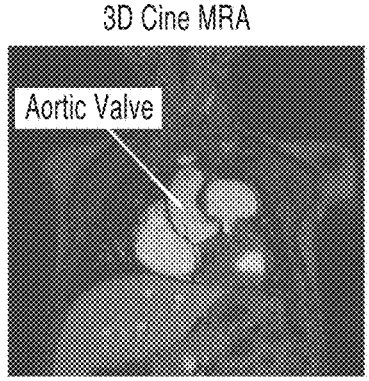
Figure 6C:
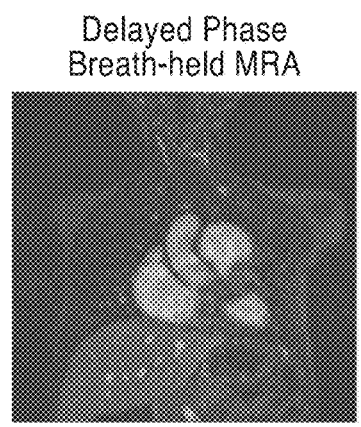

FIG. 6A through FIG. 6C are images illustrating a comparison of first-pass (FIG. 6A), 3D cine MRA (FIG. 6B), and delayed phase breath-held MRA (FIG. 6C) acquired on a 3-year-old 14 kg girl with an aneurysmal pulmonary artery. Only one of five cardiac phases is displayed, timed during the aortic ejection period. All images were acquired after ferumoxytol injection. The diaphragm of the non-breath-held 3D cine MRA image (FIG. 6B) has a sharp border (including good delineation of the aortic valve leaflets (arrow)), confirming good respiratory gating using the ventilator signal. As seen in FIG. 6A through FIG. 6C, the cardiac chambers and great vessels, as well as the aortic valve and pulmonary artery, are visualized better using the 3D cine MRA. First-pass and delayed-phase breath-held MRA images (FIG. 6A and FIG. 6C) show blurring of the heart and proximal great vessels (poor definition in the cardiac chambers and aortic outflow) due to cardiac motion.

Figure 7A:
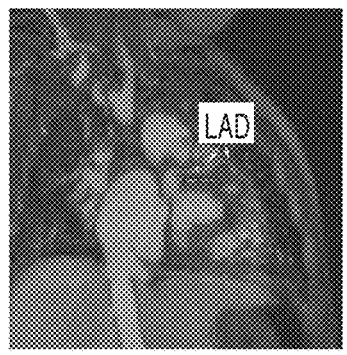
FIG. 7A through FIG. 7C show images of all three major branches of the coronary artery (left anterior descending (FIG. 7A), left circumflex (FIG. 7B) and right coronary arteries FIG. 7C) clearly visualized by reformatting the 3D cine MRA data acquired in an 8-month-old 7 kg boy with 0.9 mm isotropic resolution.
Figure 7B:
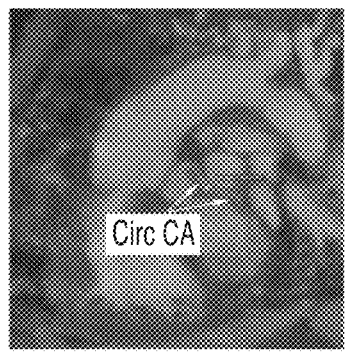
Figure 7C:
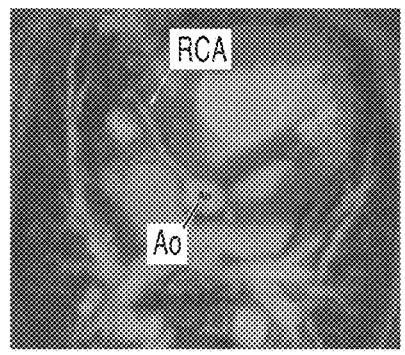

The 3D isotropic resolution of the 3D cine MRA sequence allows for arbitrary multi-planar reformatting of the volume. FIG. 7A through FIG. 7C show images of all three major branches of the coronary artery (left anterior descending (LAD—FIG. 7A), left circumflex (Circ CA—FIG. 7B) and right coronary artery and aorta (RCA, Ao—FIG. 7C) clearly visualized (demonstrating excellent delineation of the left and right coronary arteries previously not possible using conventional breath-held MRA) by reformatting the 3D cine MRA data acquired in an 8-month-old 7 kg boy with 0.9 mm isotropic resolution. In 5 out of the 6 patients, the origins of the coronaries, including 2 anomalous origins, were identified based on the 3D cine MRA image.

As shown in Table 1, the subjective image score of the 3D cine MRA was significantly higher than conventional first-pass MRA at coronary origin (p=0.029), aortic root (p=0.001), myocardium (p=0.029) and pulmonary trunk (p=0.043). The scores on descending aorta matched those of the first-pass MRA, although respiratory-gating, instead of breath-holding, was used in the 3D cine MRA method.

The 3D cine MRA method provided significantly higher SNR over the conventional MRA (91.4±10.7 vs. 72.0±10.3, P=0.034). FIG. 8A and FIG. 8B illustrate how the vessel sharpness was measured on the subjects aorta and left ventricle, respectively. Images 130 and 140 show aorta and left ventricle images respectively for conventional first-pass MRA lines 136, 146. Images 132 and 142 show aorta and left ventricle images respectively for 3D cine MRA lines 134, 144. When compared with the conventional first-pass MRA, the 3D cine MRA had significantly higher (better) vessel sharpness measurements at ascending aorta (P=0.005) and the LV (P=0.002).

The above results suggest that, by using ferumoxytol in children of any age undergoing cardiovascular MR imaging with controlled ventilation, it is feasible to acquire detailed, high resolution cine MR angiograms without the need for breath holding. In our initial study, the quality of the gated cine MR angiograms was at least as good as the breath held angiograms for vascular structures that do not undergo cardiac related motion, and was significantly better for all structures which are subject to cardiac motion. We were able to resolve cardiac and vascular anatomy with sub-millimeter isotropic resolution in multiple cardiac phases, sufficient for routine detection of coronary anatomy in patients as small as 2.5 kg.

Improved image quality compared to traditional CE-MRA approaches was realized via a combination of one or more of the following: 1) Ferumoxytol was used as an intravascular contrast agent, which relaxes the requirement for "first-pass" acquisition and thus enables an ECG-triggered CE-MRA scan of several minutes without breath-holding. This is especially relevant for pediatric applications because typically higher spatial resolution (hence longer scan time) is required due to the smaller size of the cardiac structures and blood vessels; 2) The ventilator circuit pressure signal served as an excellent surrogate of respiratory motion. As the patients in our study were undergoing mechanical ventilatory support, issues associated with traditional respiratory gating strategies during voluntary free-breathing are avoided, including the issue of irregular respiratory motion and drifts in the gating window; 3) the 3D cine CE-MRA sequence significantly reduced cardiac motion related blurring that is typical in standard breath-held non-cardiac-gated CE-MRA. This allowed delineation of the cardiac chambers, coronary arteries, and myocardial wall with details that were previously not possible using standard CE-MRA techniques. For pediatric patients with CHD, detailed evaluation of these structures is often crucial for the purpose of surgical planning as well as post-surgical evaluation.

Ferumoxytol, approved by the FDA for parenteral treatment of iron deficiency in chronic kidney disease patients, was shown to be a promising MRI contrast agent. The systems and methods of the present disclosure exploit the advantage of its long and stable intravascular residence time, which supports a prolonged MRA scan with motion compensation techniques during the steady-state. Furthermore, for CHD patients, it may be desirable to perform cardiovascular MRI shortly after birth. It has been reported that the glomerular filtration rate (GFR) of pre-term and term newborns can be as low as 40 ml/min/1.73 m$^2$, and it gradually increases to 66 ml/min/1.73 m$^2$ at 2 weeks after birth. For this reason, FDA advises against the use of GBCA in neonates due to concerns associated with nephrogenic systemic fibrosis. In this regard, ferumoxytol is a potential alternative MRI contrast agent for neonates.

Although the T1 relaxivity of ferumoxytol is several times higher than typical GBCA, and comparable with gadofosveset trisodium (Ablavar, Bayer Schering Pharma, Germany) in the blood pool, it has a strong T2 relaxivity (83 mM$^{-1}$second$^{-1}$ at 1.5 tesla) that is much higher than typical GBCA. In order to minimize the potential signal loss due to T2 relaxation, we used a strong partial-echo readout in our study to achieve a much shorter echo time (TE=0.9 ms). In addition to the shorter echo time, the contrast dose is chosen carefully to maximize the contrast enhancement as the signal intensity is jointly determined by the T1 shortening effect, which enhances signal, and the T2 shortening effect, which reduces signal. In one exemplary case, 4 mg/kg (0.07 mol/kg) of iron was found to provide satisfactory results for both first-pass and steady-state CE-MRA, although in this preliminary report we did not address contrast dose optimization.

The above quantitative measurement results suggest that the proposed cine CEMRA method has improved SNR over conventional first-pass CE-MRA even though a smaller voxel size is used. This is mostly because the proposed method is not limited to a breath-hold time window, and thus a longer scan time was used. In addition, the aforementioned T2 shortening effect of ferumoxytol might indirectly influence SNR using the described approach since the peak contrast agent concentration during the first-passage might cause signal loss due to enhanced T2 relaxation, offsetting the effect of the T1 shortening on signal in the standard breath-held CE-MRA. During steady state, which is when we acquired the gated cine CEMRA, the intravascular iron concentration, although stable, is lower than during the arterial first pass.

The ventilator gating approach detailed above is primarily directed to patients under general anesthesia or already intubated in the intensive care unit. However, the 3D cine CE-MRA acquisition systems and methods using ferumoxytol injection in accordance with the present disclosure can potentially be applied to patients during free-breathing using other forms of respiratory motion compensation strategies, such as diaphragm navigators, respiratory bellows or MR self-gating. It is also anticipated that a variation of the pulse sequence may be generated for pediatric patients undergoing sedation rather than general anesthesia to avoid or reduce its associated side effects and potential complications of general anesthesia.

High resolution, 3-D cine MRA in accordance with the present disclosure allows for significantly improved delineation of cardiac and central vascular anatomy in pediatric patients and has potential to supplant current techniques for anatomic and functional cardiac imaging in small children.

Example 2

Use of ferumoxytol as a contrast agent was also evaluated as a non-gadolinium alternative for high-resolution CEMRA in renal failure. 9 patients aged 6 days to 14 years were evaluated with first pass and steady state CEMRA following ferumoxytol (Feraheme, AMAG) infusion at a dose of 0.05 mmol/kg to 0.07 mmol/kg. All patients were studied on a Siemens Magnetom TIM Trio system. Coil configurations included combinations of head-neck, body array and spine array, depending on patient size. Two patients had complex congenital heart disease and 8 were being considered for organ transplantation. The patients with CHD had supplemental cardiac gated high-resolution 3D CEMRA. The imaging FOV for all sequences routinely included head, neck, thorax, abdomen and pelvis with sub-mm voxels. Multiple CEMRA phases were acquired up to 30 minutes following ferumoxytol injection and measurements of SNR and CNR in the thoracic aorta and inferior vena cava (IVC) were recorded at each phase. These were compared to similar measurements in a group of weight-matched controls examined with gadopentetate dimeglumine (Magnevist, Bayer-Schering) at 0.2 mmol/kg. Phantom measurements of T1 and T2* were made at 3.0 T over a range of ferumoxytol dilution factors to include the estimated blood concentration during first pass and steady state distribution phases.

Phantom results of relaxation times at 3.0 T vs. dilution factor for ferumoxytol were prepared. The T1 relaxivity of ferumoxytol in saline solution was approximately 9.0 mM$^{-1}$s$^{-1}$ and the T2 relaxivity was approximately 90 mM$^{-1}$s$^{-1}$. The estimated blood Fe concentration during first-pass was approximately 256× dilution of the stock ferumoxytol formulation and the steady state intravascular concentration was approximately 1000× dilution. The CNR measurements in the patient studies are summarized in Chart 1 for first pass, second phase and delayed phase. Two patients studied early in the series had signal loss in the aorta on first pass, felt to be due to too rapid injection resulting in T2* signal decay and this decreased the average value. Whereas in the magnevist group, aortic SNR decreased significantly over time, SNR in the ferumoxytol group remained stable to the last measurements, up to 35 minutes post injection. The stability of the vascular signal was felt to be advantageous for the gated CEMRA acquisitions and for venous imaging.

These findings suggest that high resolution CEMRA with ferumoxytol can be successfully performed at 3.0 T in pediatric patients with renal failure, eliminating concerns for NSF. Initial results are highly encouraging and compare favorably with Magnevist in controls.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored locally to the device in non-transitory media, or can be stored remotely such as on a server or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. A method for magnetic resonance angiography, comprising: administering an intravascular contrast agent to a human subject; acquiring a signal from a ventilatory support device coupled to the subject; acquiring cardiac magnetic resonance images of the subject; and respiratory gating the acquired cardiac magnetic resonance images as a function of the acquired signal.

2. The method of any preceding embodiment, wherein the signal comprises a ventilator airway pressure signal.

3. The method of any preceding embodiment, wherein the ventilator airway pressure signal is applied as a respiratory motion gating signal.

4. The method of any preceding embodiment, wherein the cardiac magnetic resonance images are acquired without breath-holding of the subject.

5. The method of any preceding embodiment, wherein the cardiac magnetic resonance images are acquired during the multiple passes of the contrast agent.

6. The method of any preceding embodiment, wherein the contrast agent comprises ferumoxytol.

7. The method of any preceding embodiment, wherein acquiring cardiac magnetic resonance images comprises acquiring a respiratory-gated 3D CINE MRA sequence.

8. The method of any preceding embodiment: wherein the respiratory-gated 3D CINE MRA sequence comprises a plurality of cardiac phases; and wherein respiratory gating the acquired cardiac magnetic resonance images comprises accepting or rejecting image data for each cardiac phase of the respiratory-gated 3D CINE MRA sequence.

9. The method of any preceding embodiment, wherein the 3D CINE MRA sequence comprises an ECG-triggered spoiled gradient echo sequence.

10. A system for magnetic resonance angiography, comprising: a computer processor; and a memory storing instructions executable on the processor; the instructions, when executed, performing the steps comprising: acquiring a signal from a ventilatory support device coupled to a subject; acquiring cardiac magnetic resonance images of the subject; and respiratory gating the acquired cardiac magnetic resonance images as a function of the acquired signal.

11. The system of any preceding embodiment, further comprising an intravascular contrast agent configured to be administered into the human subject.

12. The system of any preceding embodiment, wherein the signal comprises a ventilator airway pressure signal.

13. The system of any preceding embodiment, wherein the ventilator airway pressure signal is applied as a respiratory motion gating signal.

14. The system of any preceding embodiment, wherein the cardiac magnetic resonance images are acquired without breath-holding of the subject.

15. The system of any preceding embodiment, wherein the cardiac magnetic resonance images are acquired during the multiple passes of the contrast agent.

16. The system of any preceding embodiment, wherein the contrast agent comprises ferumoxytol.

17. The system of any preceding embodiment, wherein acquiring cardiac magnetic resonance images comprises acquiring a respiratory-gated 3D CINE MRA sequence.

18. The system of any preceding embodiment: wherein the respiratory-gated 3D CINE MRA sequence comprises a plurality of cardiac phases; and wherein respiratory gating the acquired cardiac magnetic resonance images comprises accepting or rejecting image data for each cardiac phase of the respiratory-gated 3D CINE MRA sequence.

19. The system of any preceding embodiment, wherein the 3D CINE MRA sequence comprises an ECG-triggered spoiled gradient echo sequence.

20. A system for magnetic resonance angiography, comprising: an intravascular contrast agent configured to be administered into a human subject; a ventilatory support device coupled to a subject; a computer processor; and a memory storing instructions executable on the processor; the instructions, when executed, performing the steps comprising: acquiring a signal from a ventilatory support device; acquiring cardiac magnetic resonance images of the subject; and respiratory gating the acquired cardiac magnetic resonance images as a function of the acquired signal.

21. The system of any preceding embodiment, wherein the signal comprises a ventilator airway pressure signal that is applied as a respiratory motion gating signal.

22. The system of any preceding embodiment, wherein the contrast agent comprises ferumoxytol.

23. The system of any preceding embodiment, wherein acquiring cardiac magnetic resonance images comprises acquiring a respiratory-gated 3D CINE MRA sequence.

24. The system of any preceding embodiment: wherein the respiratory-gated 3D CINE MRA sequence comprises a plurality of cardiac phases; and wherein respiratory gating the acquired cardiac magnetic resonance images comprises accepting or rejecting image data for each cardiac phase of the respiratory-gated 3D CINE MRA sequence.

25. The system of any preceding embodiment, wherein the 3D CINE MRA sequence comprises an ECG-triggered spoiled gradient echo sequence.

26. A method for non-gadolinium based high-resolution CEMRA for evaluation of renal failure in a patient, comprising: administering ferumoxytol as a contrast agent into the subject, and performing high-resolution CEMRA on the patient.

27. A system for non-gadolinium based high-resolution CEMRA, comprising: a ferumoxytol-based contrast agent configured to be administered into a human subject; a memory storing instructions executable on the processor; and the instructions, when executed, performing the steps comprising: acquiring high-resolution CEMRA images of the subject.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

acquiring a signal from a ventilatory support device coupled to the subject;

acquiring cardiac magnetic resonance images of the subject using a respiratory-gated 3D CINE MRA sequence, wherein the respiratory-gated 3D CINE MRA sequence comprises a plurality of cardiac phases;

regulating a respiratory pattern of the ventilatory support device; and respiratory gating the acquired cardiac magnetic resonance images as a function of the acquired signal, wherein respiratory gating the acquired cardiac magnetic resonance images comprises accepting or rejecting image data for each cardiac phase of the respiratory-gated 3D CINE MRA sequence.

2. A method as recited in claim 1, wherein the signal comprises a ventilator airway pressure signal.

3. A method as recited in claim 2, wherein the ventilator airway pressure signal is applied as a respiratory motion gating signal.

4. A method as recited in claim 1, wherein the cardiac magnetic resonance images are acquired without breath-holding of the subject.

5. A method as recited in claim 1, wherein the cardiac magnetic resonance images are acquired during the multiple passes of the contrast agent.

6. A method as recited in claim 1, wherein the contrast agent comprises ferumoxytol.

7. A method as recited in claim 1, wherein the 3D CINE MRA sequence comprises an ECG-triggered spoiled gradient echo sequence.

8. A system for magnetic resonance angiography, comprising:

a computer processor; and a memory storing instructions executable on the processor;

the instructions, when executed, performing the steps comprising:

acquiring a signal from a ventilatory support device coupled to a subject;

acquiring cardiac magnetic resonance images of the subject using a respiratory-gated 3D CINE MRA sequence, wherein the respiratory-gated 3D CINE MRA sequence comprises a plurality of cardiac phases;

regulating a respiratory pattern of the ventilatory support device; and

TABLE 1

| | Subjective Image Quality Score | | | | |
|---|---|---|---|---|---|
| | Coronary Origin | Aortic Root | Myocardium (LV and RV) | Pulmonary Trunk | Descending Aorta |
| Mean ± S.D First-pass MRA | 1.25 ± 0.43 | 1.75 ± 0.43 | 2.25 ± 0.43 | 2.75 ± 0.43 | 4.00 ± 0.00 |
| Mean ± S.D 3D cine MRA | 2.83 ± 0.69 | 3.33 ± 0.47 | 3.67 ± 0.47 | 3.80 ± 0.40 | 4.00 ± 0.00 |
| P-value | 0.029 | 0.001 | 0.029 | 0.043 | 1 |

What is claimed is:

1. A method for magnetic resonance angiography, comprising:

administering an intravascular contrast agent to a human subject;

respiratory gating the acquired cardiac magnetic resonance images as a function of the acquired signal, wherein respiratory gating the acquired cardiac magnetic resonance images comprises accepting or rejecting image data for each cardiac phase of the respiratory-gated 3D CINE MRA sequence.

9. A system as recited in claim 8, further comprising an intravascular contrast agent configured to be administered into the human subject.

10. A system as recited in claim 8, wherein the signal comprises a ventilator airway pressure signal.

11. A system as recited in claim 10, wherein the ventilator airway pressure signal is applied as a respiratory motion gating signal.

12. A system as recited in claim 8, wherein the cardiac magnetic resonance images are acquired without breath-holding of the subject.

13. A system as recited in claim 8, wherein the cardiac magnetic resonance images are acquired during the multiple passes of the contrast agent.

14. A system as recited in claim 8, wherein the contrast agent comprises ferumoxytol.

15. A system as recited in claim 8, wherein the 3D CINE MRA sequence comprises an ECG-triggered spoiled gradient echo sequence.

16. A method for magnetic resonance angiography, comprising:
 administering an intravascular contrast agent to a human subject;
 acquiring a signal from a ventilatory support device coupled to the subject;
 acquiring cardiac magnetic resonance images of the subject using a respiratory-gated 3D CINE MRA sequence, wherein the respiratory-gated 3D CINE MRA sequence comprises a plurality of cardiac phases, and wherein the 3D CINE MRA sequence comprises an ECG-triggered spoiled gradient echo sequence;
 regulating a respiratory pattern of the ventilatory support device; and
 respiratory gating the acquired cardiac magnetic resonance images as a function of the acquired signal, wherein respiratory gating the acquired cardiac magnetic resonance images comprises accepting or rejecting image data for each cardiac phase of the respiratory-gated 3D CINE MRA sequence.

17. A method as recited in claim 16, wherein the signal comprises a ventilator airway pressure signal.

18. A method as recited in claim 17, wherein the ventilator airway pressure signal is applied as a respiratory motion gating signal.

19. A method as recited in claim 16, wherein the cardiac magnetic resonance images are acquired without breath-holding of the subject.

20. A method as recited in claim 16, wherein the cardiac magnetic resonance images are acquired during the multiple passes of the contrast agent.

21. A method as recited in claim 16, wherein the contrast agent comprises ferumoxytol.

22. A system for magnetic resonance angiography, comprising:
 a computer processor; and
 a memory storing instructions executable on the processor;
 the instructions, when executed, performing the steps comprising:
  acquiring a signal from a ventilatory support device coupled to a subject;
  acquiring cardiac magnetic resonance images of the subject, using a respiratory-gated 3D CINE MRA sequence, wherein the respiratory-gated 3D CINE MRA sequence comprises a plurality of cardiac phases, and wherein the 3D CINE MRA sequence comprises an ECG-triggered spoiled gradient echo sequence;
  regulating a respiratory pattern of the ventilatory support device; and
  respiratory gating the acquired cardiac magnetic resonance images as a function of the acquired signal, wherein respiratory gating the acquired cardiac magnetic resonance images comprises accepting or rejecting image data for each cardiac phase of the respiratory-gated 3D CINE MRA sequence.

23. A system as recited in claim 22, further comprising an intravascular contrast agent configured to be administered into the human subject.

24. A system as recited in claim 22, wherein the signal comprises a ventilator airway pressure signal.

25. A system as recited in claim 24, wherein the ventilator airway pressure signal is applied as a respiratory motion gating signal.

26. A system as recited in claim 22, wherein the cardiac magnetic resonance images are acquired without breath-holding of the subject.

27. A system as recited in claim 22, wherein the cardiac magnetic resonance images are acquired during the multiple passes of the contrast agent.

28. A system as recited in claim 22, wherein the contrast agent comprises ferumoxytol.

* * * * *